United States Patent [19]
Willem et al.

[11] Patent Number: 5,934,283
[45] Date of Patent: Aug. 10, 1999

[54] PUBOVAGINAL SLING DEVICE

[75] Inventors: Germain E. Willem, Tremelo, Belgium; Christopher Harris, Roemond, Netherlands; Susan J. Hartjes-Doherty, Eden Prairie; Daniel G. Holman, Minneapolis, both of Minn.

[73] Assignee: Uroplasty, Inc., Minneapolis, Minn.

[21] Appl. No.: 08/839,777

[22] Filed: Apr. 15, 1997

[51] Int. Cl.⁶ .................................................... A61F 5/48
[52] U.S. Cl. ................................ 128/885; 604/55; 600/29
[58] Field of Search ..................... 600/30, 29; 604/358, 604/385.1, 55; 128/885; 606/151

[56] References Cited

U.S. PATENT DOCUMENTS

| | | | |
|---|---|---|---|
| 1,328,176 | 1/1920 | Martinka | 120/5 |
| 3,789,828 | 2/1974 | Schulte | 600/30 |
| 4,456,589 | 6/1984 | Holman et al. | 424/95 |
| 5,036,867 | 8/1991 | Biswas | 600/30 |
| 5,549,619 | 8/1996 | Petus et al. | 606/151 |

OTHER PUBLICATIONS

Eisaburo Imamura, et al., "Epoxy compunds as a New Cross–linking Agent for Porcine Aortic Leaflets: Subcataneous Implant Studies in Rats", Journal of Cardiac Surgery, vol. 4, No. 1, Mar. 1989, pp. 50–57.

Y. Noishiki et al., "Development of a Small Caliber Vascular Graft by a New Crosslinking Method Incorporating Slow Heparin Release Collagen and Natural Tissue compliance", ASAIO Trasactions, vol. 32, No. 1, Jul.–Sep. 1986, pp. 114–119.

Takafumi Okoshi et al., "Long–term Results of a New Antithrombogenic Cardiac Wall Substitute", ASAIO Transactions, vol. XXXV., 1989, pp. 391–395.

Robert Peterson et al., "Dynamic Internal Compliance Measurements of Fresh and Fixed Artery", ASAIO Transactions, Jul.–Sep., No. 3, 1990, pp. M766–M769.

Yuichiro Murayama et al., "Reduction of the Antigenicity and Immunogenicity of Xenografts by a New Cross–linking Reagent", ASAIO Transactions, vol. XXXIV., 1989, pp. 546–549.

*Primary Examiner*—Wynn Wood Coggins
*Assistant Examiner*—N. Kent Gring
*Attorney, Agent, or Firm*—Arnold, White & Durkee; Jonathan D. Spangler

[57] ABSTRACT

A sling device for surgical implantation into human recipient to support the urethra, the sling including an elongated strip of supple material. The elongated strip has a center portion, opposite first and second side portions, and a slot passing through the center portion, through which one of the side portions can pass, thereby forming a loop in the elongated strip. The material is a biological acceptable material for implantation into the human recipient, preferably selected from the group consisting of synthetic polymers, processed animal tissues, and combination thereof. A method of reducing the incidence of involuntary urination or restoring urinary continence in an incontinent human subject is also disclosed, including the steps of providing a sling device of the type previously described and surgically implanting the sling device in the human subject so that the urethra is biased upward so as to elevate the urethra.

31 Claims, 2 Drawing Sheets

PUBOVAGINAL SLING DEVICE

FIELD OF THE INVENTION

The present invention relates to surgically implanted devices to provide urethral and pelvic support for urogenital organs, particularly female urogenital organs, in an attempt to restore urinary continence.

BACKGROUND OF THE INVENTION

Urinary incontinence is a wide spread disorder. It is particularly disconcerting to those who suffer from the disorder, and often times demeaning when sufferers are confronted with the reality that they may need to be catheterized for an extended period of time, perhaps indefinitely.

Stress incontinence is a relatively common disorder among post-menopausal women. This disorder often results from prior injuries occurring during child birth. At least some of the women suffering this disorder seek surgical solutions to restore urinary continence so that catheterization will be unnecessary. As women from the post-war baby boom generation advance in age, it is believed that the number of women seeking such solutions will increase.

One such surgical solution, which has been used in the past, is to implant a pubovaginal sling to provide urethral and pelvic support for the female urogenital organs in an attempt to restore urinary continence. The sling is used to raise the urethra and support it, and to enable the urethra to remain closed under fluid pressure from the bladder. C. Mason et al., American Urological Association, Annual Convention, 1996, report that pubovaginal sling cystourethropexy has become the "mainstay" of surgical therapies for Type III Stress Urinary Incontinence (SUI). However, many patients undergoing this procedure are reported to be plagued with unexpected urinary retention or detrusor instability post-operatively. F. E. Govier, American Urological Association, Annual Convention, 1996, reports the management of Intrinsic Sphincteric Deficiency (ISD) by constructing a pubovaginal sling from existing tissues within the patient's body. Dr. Govier treated a number of female patients having urodynamically-proven ISD. A pubovaginal sling was created using a portion of the fascia lata from each of the respective patients. An unscarred facial strip approximately 20–24 cm by 2.5 cm was obtained by making several incisions in the patient's thigh in order to provide material for the sling. The sling was attached to itself over a 3–4 cm bridge of the rectus fascia. This treatment was reported to provide excellent results due in part to advantages provided by the length the strip of fascia lata, which was reportedly long enough to be attached to itself to enable the surgeon to provide sufficient tension to the sling to obtain the desired result. The uniform thickness and width of the graft was also reported to allow for excellent urethral closure, minimizing the chance of obstruction. Furthermore, since the procedure did not involve an abdominal incision, it was reported that hospital stays were relatively short, that full activity was achievable at two weeks and that there was little or no post-operative chance of an abdominal wall hernia resulting from the procedure.

It will be appreciated, however, that other solutions which do not require the use of autologous tissues will be desirable to some patients. This is especially because the surgical removal of such tissue is not required. In addition, autologous tissues may go through undesirable changes that will not occur in other materials. Furthermore, selecting and shaping the strip may require considerable skill which may not be within the capability of all surgeons conducting the procedure.

Accordingly, it will be appreciated that there remains a need for an efficient, price competitive pubovaginal sling device which will be an improvement over the previously mentioned slings and other prior art devices. The present invention also provides advantages over the prior art methods for manufacturing sling devices, methods of surgically restoring urinary continence, and also offers other advantages over the prior art and solves other problems associated therewith.

SUMMARY OF THE INVENTION

Accordingly, it is an object of the present invention to provide a low cost pubovaginal sling device which can be made uniformly available to surgeons for use in surgically restoring urinary continence. The present pubovaginal sling device for surgical implantation in a human recipient comprises an elongated strip of supple material. The elongated strip has a center portion and opposite first and second side portions. The center portion includes a slot through which one of the respective side portions can pass, thereby forming a loop in the elongated strip. The material is a biologically acceptable material for implantation into the recipient. In preferred embodiments, the material is selected from the group consisting of synthetic polymers, processed animal tissues and combinations thereof, each of which are suitable for implantation into the human recipient. In preferred embodiments, where the material is a processed animal tissue, the preferred tissue is selected from the group consisting of porcine tissue, bovine tissue, ovine tissue, equine tissue and human tissue; the human tissue preferably coming from human cadavers. The processed animal tissue is preferably made from a tissue selected from the group consisting of tendons, ligaments and fibro serous tissues. In preferred embodiments where the processed animal tissue is made from fibro serous tissues, these tissues will preferably be selected from the group consisting of dura mater, pericardium, peritoneum, tunica vaginalis and dermas. These tissues are preferably processed by being cleansed, dehydrated, cross-linked and sterilized.

In a preferred embodiment, the pubovaginal sling device for surgical implantation, preferably comprises an elongated strip of material having variable dimensions, including a thickness, a width and a length. The length is preferably greater than the width, and the width is preferably greater than the thickness. The preferred elongated strip has a center portion and opposite first and second side portions interconnected with and extending away from the center portion. The side portions preferably include an extending limb and a looping limb, the looping limb having a smallest width which is less than a largest width of the center portion. The center portion preferably includes a slot through which the looping limb can pass, thereby forming a loop in the elongated strip. Preferably, the material is a supple material which is sterile or can be effectively sterilized, and is otherwise biologically acceptable for implantation into a human recipient.

The present invention also includes a method of reducing the incidence of involuntary urination in an incontinent human subject, or, alternatively, restoring urinary continence in such a subject. The incontinent human subject is a woman having an urethra, other internal tissues in general proximity to the urethra and an abdominal rectus sheath. The method includes the steps of: (1) providing a sling device for surgical implantation into the human subject, the sling device including an elongated strip of supple material, the strip having a center portion and opposite side portions, the center portion having a slot through which one of the side portions can pass thereby forming a loop in the elongated strip, the material being biologically acceptable for implantation into the human subject; and (2) surgically implanting the sling device in the incontinent human subject such that one the side portions passes through the slot to form a loop which encircles the urethra, where in the respective side portions encircle the other internal tissues and preferably, the abdominal rectus sheath, the side portions being fixed together such that sufficient tension exists upon the respective side portions to restrain the loop in such a manner that the urethra is biased upward, closer to the other internal tissues and the abdominal rectus sheath within the human subject so as to elevate the urethra relative to a prior untensioned position within the human subject when the human subject is in a standing position, thereby preferably minimizing the instances of involuntary urination or incontinence within the human subject.

It is an object of the present invention to provide a biologically compatible pubovaginal sling device which can be made uniformly available to surgeon during pubovaginal sling cystourethorpexy. The present device can be made of a number of materials all of which are biologically acceptable and relatively easy to sterilize. Preferred materials include processes animal tissues, but synthetic materials may also be used as well as combinations of synthetic materials and animal tissues which are chemically cross-linked.

As used herein, the following terms and/or phases have the indicated meanings. The terms "processed animal tissue" mean tissue from animal sources which has been "cross-linked" either chemically or both other means, wherein antigenic sites within the tissue are bound so as to reduce the antigenicity of the tissue. "Animal cells" means cells originating from an animal source. The phrase "bias the urethra upward" means to support the urethra of the subject from an underside of the urethra so that the urethra is elevated at least somewhat from an unsupported position which would be occupied by the urethra when the subject is in standing upright.

These and various other advantages and features of novelty which characterize the present invention are pointed out with particularity in the claims annexed hereto and forming a part hereof. However, for a better understanding of the present invention, its advantages and other objects obtained by its use, reference should be made to the drawings, which form a further part hereof, and to the accompanying descriptive matter, in which there is illustrated and described preferred embodiments of the present invention.

BRIEF DESCRIPTION OF THE DRAWINGS

In the drawings, in which like reference numerals indicate corresponding parts of the present invention throughout the several views.

DETAILED DESCRIPTION OF THE PREFERRED EMBODIMENTS

Figure 1:
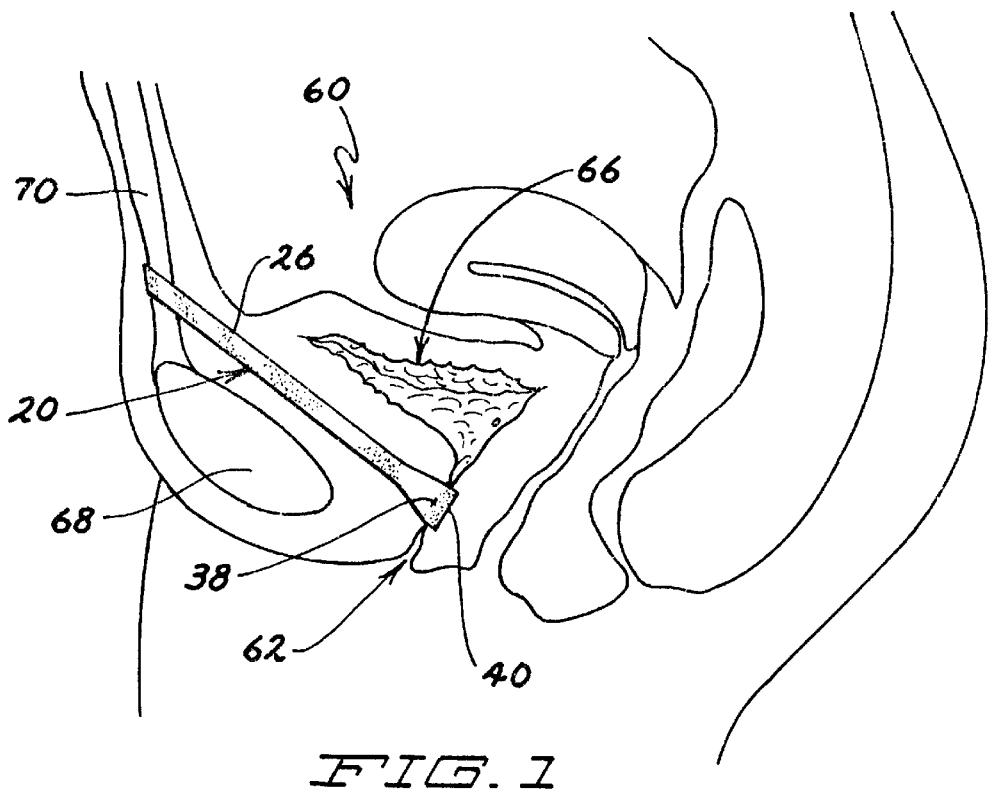
FIG. 1 is a schematic illustration of a pubovaginal sling of the present invention in place within a female patient shown in partial cross-section.

Referring now to the drawings, and specifically to FIGS. 1–4, the pubovaginal sling device 20 of the present invention can be made of any of number of biologically compatible materials and provided to surgeons in various dimensions for surgical implantation in human subjects 60. In preferred embodiments, the width and length of the sling 20 may be varied in preparation for a surgical procedure by removing a portion or portions of uniformly sized sling devices 20 provided commercially by a manufacturer of the sling device 20.

The preferred sling 20 is used to provide urethral and pelvic support to female urogenital organs, preferably the urethra and/or bladder neck in an attempt to restore urinary continence in incontinent women. The device 20 works in a manner similar to that of other sling devices known in the art. However, the present device 20 provides a loop support 40 around the urethra 62, preferably the mid-urethra and/or bladder neck, which is not provided by other sling devices. In preferred embodiments, made from processed animal tissues, the present sling device 20 provides superior strength and flexibility, such that superior is postoperative results can be anticipated.

Figure 2:
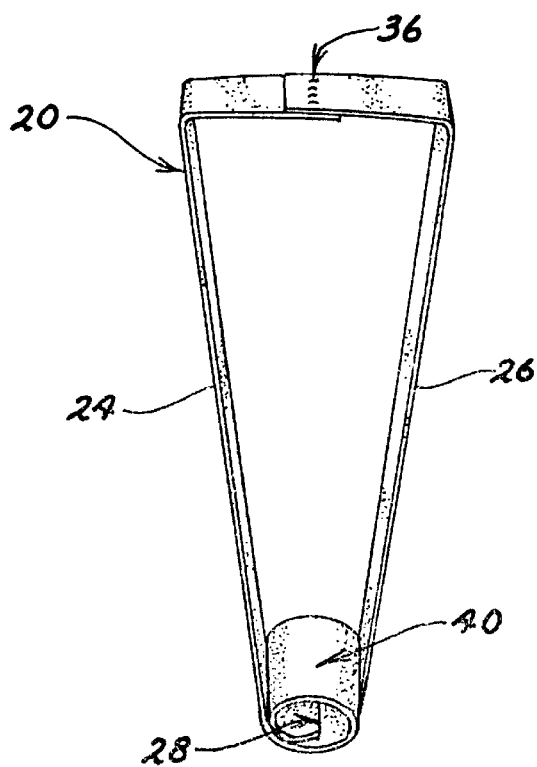
FIG. 2 is a perspective view of the pubovaginal sling shown in FIG. 1 as it would appear in place within the subject's body following surgical implantation, but without showing the parts of subject's body.
Figure 3:
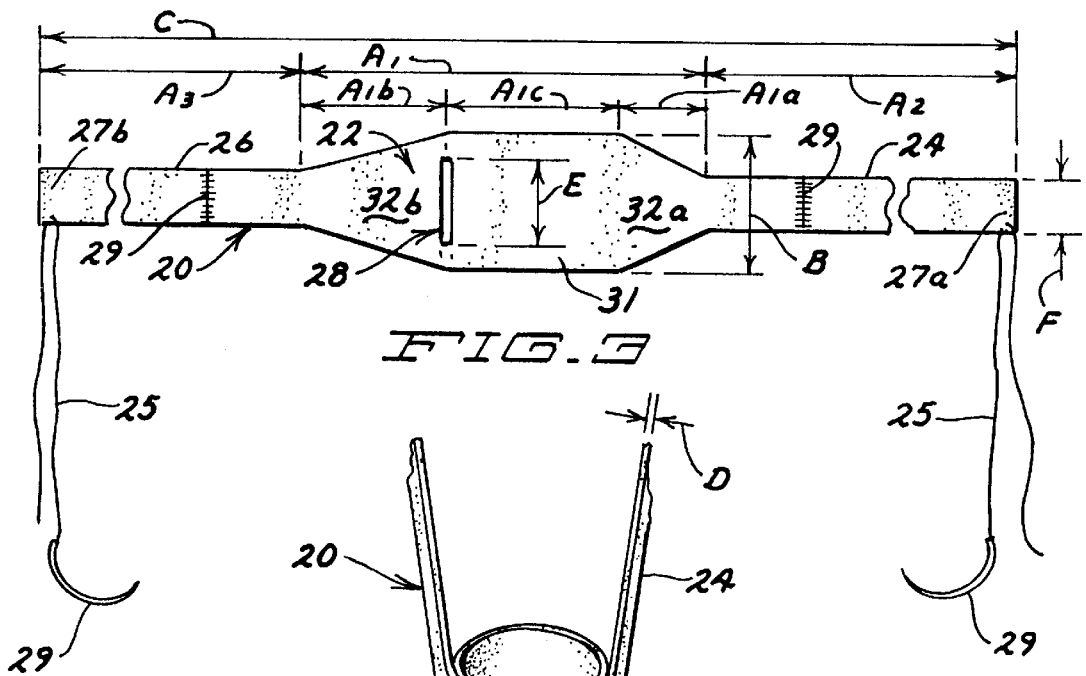
FIG. 3 is a plan view of a pubovaginal sling of the present invention similar to that shown in FIGS. 1 and 2.

The pubovaginal sling 20 of the present invention includes a center portion 22 and first and second side portions 24 and 26, respectively. The center portion includes a slot 28 through which the first side portion or looping limb 24 may pass to form a loop 40 in the elongated sling device or strip 20. In preferred embodiments of the present device made of processed animal tissues, and the respective side portions may include an additional piece or pieces of processed animal tissue which are joined to other portions of the elongated strip by any of a number of well known attachment methods, preferably by securing the attached piece or pieces to the other portions of the elongated strip 20 using sutures 29 as shown in FIG. 3. By joining separate pieces of processed animal tissue in this way, it is possible to obtain a longer strip than might otherwise be available when made from any particular material from which the strip may be made. Where the length of available materials is not as limited as it may be in certain cases when utilizing processed animal tissues, the preferred sling device 20 will not have the multiple pieces or sutures joining multiple pieces together. In this particular case, therefore, the embodiment of the sling 20 shown in FIG. 3 is illustrative only, and is not meant to limit the present invention to sling devices having multiple pieces joined together, as opposed to a single elongated strip as illustrated in FIGS. 1, 2 and 3. In many preferred embodiments the sling device 20 will be a single piece of material. In circumstances where sufficiently elongated processed animal tissues are available, preferred sling devices of the present invention made of such materials will be without separate pieces or suture lines.

Referring now especially to FIG. 3, in preferred embodiments, the center portion 22 has a length $A_1$, and a width B. In such embodiments the sling device 20 will have a length C and a variable thickness D. The center portion 22 will preferably have a main section 31 having a length $A_{1c}$ and shoulder sections 32a and 32b, having lengths $A_{1a}$ and $A_{1b}$, interconnecting the main section 31 to the side portions 24 and 26 on either side of the main section 31, respectively. The slot 28 has a length E which is greater than the width F of the looping limb 24, such that the looping limb 24 can pass easily through slot 28 to form a loop support 40 which can encircle a urethra 62 of a subject and enable the attending surgeon to lift or elevate the urethra 62, and preferably the bladder neck 64 as well, by placing appropriate tension on the sling 20 when it is implanted within the subject. The respective shoulders 32a and 32b preferably have a variable width which increases as the shoulders 32a and 32b extend from the respective side portions 24 and 26 toward the main section 31. The length of the respective side portions 24 and 26 are denoted by dimension lines $A_2$ and $A_3$ respectively. As is evident from reviewing the sling 20 illustrated in FIG. 3, the width F of the looping limb 24 is less than the length E of the slot 28, which is, in turn, less than the greatest width B of the center portion 22. It will be appreciated that it is unnecessary for the various dimensions of the sling 20 and its various sections or parts to be constant and that these dimensions may vary even in a single embodiment. It will also be appreciated, that the length C of the sling 20 will be greater than the greatest width B of the sling 20, and the greatest width B of the sling 20 will be greater than the greatest thickness D of the sling 20. In preferred embodiments, the respective shoulders 32a and 32b will have a variable width which increases as the measurement is made moving from the end proximate the respective side portion 24 or 26 to the main section 31, or from a width the same or similar to the width F of the side portion 24 or 26 to the width B of the main section 31.

Figure 5:
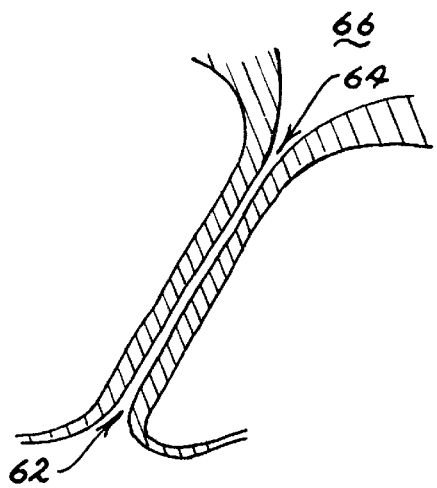
FIG. 5 is a schematic cross-sectional view of a urethra of a stress incontinent female subject showing the open urethra in an unsupported position as is common in a stress incontinent subject when the subject is standing upright.
Figure 6:
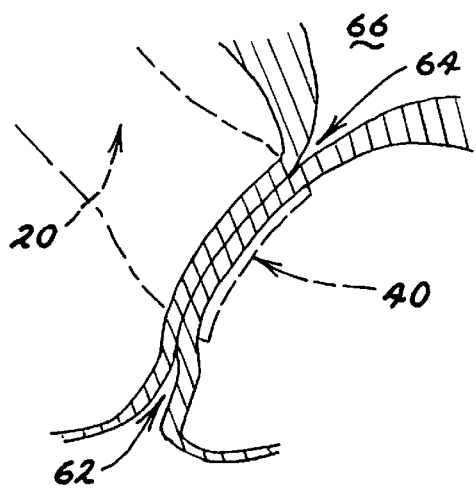
FIG. 6 is a schematic cross-sectional view of a urethra of a female subject similar to that shown in FIG. 5, except that the urethra shown in FIG. 6 has been surgically elevated by engagement with a pubovaginal sling of the present invention (shown in phantom) which encircles the urethra in the manner depicted in FIGS. 1, 2 and 4, and biases the urethra upward, closer to other internal tissues (not shown) within the human subject so as to elevate the urethra relative to the prior position of the urethra when the subject is in standing position similar to that shown in FIG. 5.

Referring now also to FIGS. 5 and 6, the preferred sling device 20 is preferably used to provide an anchored urethral loop 40 around the urethra 62 and/or bladder neck 64 of the subject. The suggested surgical procedure is intended to provide correction in the form of support for the urethra 62 and bladder neck 64 by elevation and repositioning of the urethra 62 and bladder neck 64 as shown in FIG. 6. The position of the urethra 62 prior to the procedure is illustrated in FIG. 5. In FIG. 6, it will be noted that the urethra 62 is lifted or elevated and is curved upward somewhat more than depicted in FIG. 5, prior to descending further away from the bladder 66 and bladder neck 64.

Preferred embodiments of the pubovaginal sling device 20 of the present invention will have the following dimensions: (1) length: C=530 mm; $A_1$=70 mm; $A_2$=230 mm; $A_3$=230 mm; $A_{1c}$=30; $A_{1b}$=25 mm; $A_{1a}$=15 mm; and E=15 mm (length of the slot 28); (2) width: F=10 mm; B=25 mm; and (3) thickness: D=10 mm. The thickness may be from about 0.1 to about 2.0 mm or more; preferably about 0.1 to about 1.0 mm; and may in some cases vary somewhat, especially in material from animal sources. It will be appreciated that the dimensions of the sling 20 will vary, however, and in many cases, vary proportionately.

The length of the urethra 62 in women is believed to vary from about 10 mm to about 50 mm, preferably about 15 mm to about 40 mm. For some subjects a sling 20 having a small width B of 15 mm may be desirable. Such slings 20 will be made proportionally smaller in all of the width and length dimensions set forth herein above, but the thickness D will not be varied substantially, if at all. Similarly, if the width B is set at 20 mm, the other length and width dimensions will be sized up or down proportionately. The width B can be from about 5 mm to about 40 mm, preferably about 10 mm to about 30 mm, more preferably about 15 mm to about 25 mm. Obviously, any of these dimensions can vary as desired at the time of manufacture or use.

The surgical procedure is generally initiated by applying some form of anesthesia to the female patient 60. Although local anesthesia is preferred, the operation can be conducted under general anesthesia. A Foley urethra catheter is generally inserted preoperatively into the bladder 66 of the subject through the urethra 62. The procedure is initiated by making two horizontal incisions; a horizontal abdominal incision just above the pubis 68, and a vaginal incision, in the vaginal orifice, on the upper surface of the vaginal wall approximately 0.5 to about 1 cm below the external urethral meatus. Blunt dissection of the pubourethral ligaments, the urethra 62 and the bladder neck 64 from the anterior vaginal wall and surrounding tissues will then proceed. The horizontal incision is made just above the pubis 68 across the midline and dissected down to the abdominal rectus sheath 70, preferably insuring that all of the subcutaneous fat is removed from the sheath 70. Left lateral blunt dissection then proceeds from the vaginal incision up through the retro pubic space, through the abdominal rectus sheath 70 into the supra pubic incision, followed by right lateral blunt dissection from the vaginal incision up through the retro pubic space through the abdominal rectus sheath 70 into the supra pubic incision. The second side portion or left limb 26 of the preformed sling device 20 is then fed through the vaginal incision, the recto pubic tunnel created by the left lateral blunt dissection, and through the abdominal rectus sheath 70 to the supra pubic incision. The right limb or looping limb 24 is then fed through the vaginal incision, around the dissected urethra 62, through the slot 28 in the center portion 22 of the sling 20, up through the retro pubic tunnel created by the right lateral blunt dissection, through the rectus sheath 70 and through the supra pubic incision. Care is then taken to properly size the loop support 40 created when the looping limb 24 is passed through the slot 28, and sutures 38 are then placed through the overlapping segments of the sling 20 on the opposite lateral sides of the loop support 40 to ensure that the loop support 40 does not diminish in cross-sectional diameter during its residence within the body 60. The respective side portions or limbs 24 and 26 are overlapped supra over the abdominal rectus sheath 70; tension is placed upon the left and right limbs 26 and 24 by bringing them together over the sheath 70 until the urethra 62 is raised or elevated to the desired position providing appropriate support to the urethra 62, and an appropriate amount of tension is placed upon the urethra 62 so that it will remain in the desired position. The respective limbs 26 and 24 are then clamped in place, preferably with a blunt tissue forceps or the like, and fixated using any of a number of means which are well known in the surgical arts, preferably a "running mattress" suture or such other fixation mechanism as may be desired. The vaginal and abdominal incisions are subsequently closed in a conventional manner.

Figure 4:
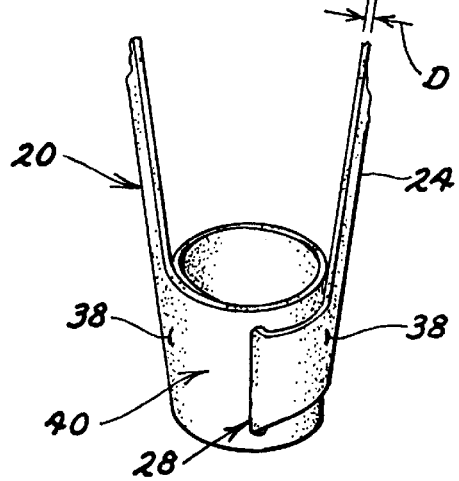
FIG. 4 is a perspective view of a cut-away of the loop portion of the pubovaginal sling shown in FIG. 2, but from below the loop portion of the elongated strip.

The schematic illustration provided in FIG. 1 diagrammatically depicts the sling support device 20 in place following implantation, encircling the urethra, and passing behind the pubic bone 68 to the rectus abdominis fixation or suture 36 above the pubic bone 68 supra the abdominal rectus sheath 70. The urethra/bladder neck loop 40 preferably has sutures 38 fixating the loop 40 on either lateral side as shown in FIG. 4.

In the embodiment shown in FIG. 3, the sling device 70 includes a length of a non-absorbable suture material 25 in each of the ends 27a and 27b of the respective right and left side portions or limbs 24 and 26. In preferred embodiments, the suture material 25 will be engaged with suture needles 29 which can be fed through the vaginal incision, and ultimately up to the supra abdominal incision. The respective limbs or side portions 26 and 24 can then be drawn up through the abdominal incision and subsequently fixed together. Alternatively, a blunt forceps may be used to reach through the abdominal incision to grasp the suture material 25, and preferably, the suture needle 29, to draw the suture material 25 and the respective limb or side portion 24 or 26 up from the vaginal incision. When the suture material 25 is present, the left limb 26 is drawn up through the abdominal incision first. The suture material 25 engaged with the right limb or looping limb 24 is then fed around the urethra 62 and through the slot 28, and the right limb 24 is subsequently drawn around the urethra 62 and through the slot 28. A blunt forceps may then be used to draw the suture material 25 and the looping limb 24 up through the abdominal incision. Sutures 38 to secure the urethral/bladder neck loop 40 may then be secured and the rectus abdominis fixation 36 may be created as previously described, after appropriate tension is placed upon the urethra 62.

In preferred embodiments, the non-absorbable suture material used for suture material 25, sutures 38 and the preferred running mattress sutures or the like in the rectus abdominis fixation 36 will be a non-absorbable suture material which is well known in the art such as polyester, preferably Dacron® polyester, expanded polytetrafluoroethylene (EPTFE), preferably Gore-Tex®, polypropylene, braided silk, or the like.

As stated above, the material used to manufacture the slings 20 of the present inventions include synthetic polymers, processed animal tissues, combination thereof, and the like. The synthetic polymers include polymers such as polytetrafluoroethylene (PTFE), preferably Teflon®; expanded polytetrafluoroethylene (EPTFE), preferably Gore-Tex®, polyesters or polyethylene terephthalates, preferably Dacron® polyester, silicone elastomers, and the like. Processed animal tissues of the present invention include processed porcine, bovine, ovine, and equine tissues, human tissues and the like. Human tissue is preferably obtained from human cadavers when used at all. These tissues are preferably selected from the group consisting of tendons, ligaments and serous membranes or fibro serous tissues, including smooth fibrous connective tissues. Preferred fibro serous tissues include dura mater, pericardium, peritoneum, tunica vaginalis and dermas.

Processed animal tissues are preferably chemically cross-linked animal tissues prepared by any of a number of methods which are well known in the art. Some of these methods are disclosed in the following documents which are hereby incorporated herein by reference: U.S. Pat. No. 4,456,589 to Holman et al.; R. C. Peterson et al., Dynamic Internal Compliance Measurements of Fresh and Fixed Arteries, ASAIO Transactions, 1990, p. M766–M769; Y. Murayama et al., Reduction of Antigenicity and Immunogenicity of Xenograpfts by a New Cross-Linking Reagent, ASAIO Trans., 1988, p. 546–549; T. Okoshi et al., Long-term Results of a New Anti-thrombogenic Cardiac Wall Substitute, ASAIO Trans., 1989, p. 391; Y. Tomizawa et al., Development of a Small-Caliber Vascular Graft with Anti-thromogenicity Induced by Extreme Hydrophilicity, ASAIO Trans., 1988, p. 644; E. Imamura et al., Epoxy Compounds As a New Cross-Linking Agent for Porcine Aortic Leaflets: Subcutaneous Implant Studies in Rats, J. Card. Surg. 1989, p. 50; and Y. Noishiki et al., Development of a Small Caliber Vascular Graft by a New Cross-Linking Method Incorporating Slow Heparin Release Collagen and Natural Tissue Compliance; ASAIO Trans., 1986, p. 114.

Preferred tissue cross-linking agents include glutaraldehyde, glutaraldehyde starch, dialdehyde, dialdehyde starch, and the like, and epoxy or polyepoxy compounds (PC) such as for example polyethelene glycol, diglycidyl ether, glycerol polyglycidyl ether, polyglycerol polyglycidyl ether, sorbitol polyglycidyl ether, and the like. Radiation may also be used to cross-link tissues from these animal sources.

Animal tissues used are preferably carefully selected from tissues available from government regulated slaughter houses where animals are known to be free of transmittable agents such as Bovine spongiform encephalopathies (BSE) and the like. Prior to treatment with chemical cross-linking agents, these tissues are preferably dehydrated with a dehydrating fluid, such as ethyl alcohol or the like, to allow for improved penetration of the chemical cross-linking agent or "tanning agent" which cross-links collagen in the tissues to both make the tissue stronger and reduce the antigenicity of the tissue. Other agents such as pepsin can also be used to further reduce antigenicity.

The cross-linking of the tissues used in the present invention is preferably accomplished using one or more of the following treatment agents: glutaraldehyde, dialdehyde, glutaraldehyde starch, dialdehyde starch, an epoxy compound or ionizing radiation. Certain processes (such as heat, radiation or pH change) or agents such as halogens, enzymes, organic solvents, detergents, sodium hydroxide, hydrochloric acid, sodium hypochlorite or hydrogen peroxide) may be used to inactivate viruses with and without protein coats or to destroy BSE agent infectivity during the manufacturing process. The tissue may also be treated with a highly volatile chemical such as for example propylene oxide, to assist with the sterilization of the tissue. Sterilization may be accomplished using one or more of the following treatments: glutaraldehyde, alcohol, propylene oxide or irradiation sterilization. The treatment of the tissue, with a combination of these materials and processes, can both cross-link the tissue and render the tissue sterile for implantation.

Combinations of synthetic polymers and processed animal tissues can also be used in slings 20 of the present invention. These combinations may include spliced strips 20 having a combination of parts, including parts made of synthetic polymers and of processed animal tissues. Such combinations also include materials which include both synthetic polymers and animal cells which are treated so as to cross-link the collagen or other commonly antigenic fibers in the animal cells. For example, materials can be used which are like the collagen coated ultrafine polyester mesh (CUFP) of the type disclosed by T. Okoski et al., ASAIO Trans., 1989, p. 391; the contents of which are hereby incorporated herein by reference.

The form of the strip of tissue allows for a minimally invasive vaginal procedure for suspending the bladder neck of the urethra. The procedure used with the strip will simplify implantation and reduce the risks associated with more invasive surgical procedures. Problems associated with suture erosion through the tissue and the potential for bone infections associated with the use of bone anchors to suspend the sling will also be reduced.

Processed pericardial tissue has both a smooth and rough surface. It is the intention of the inventors that the rough surface of the tissue will be adjacent to the tissue surrounding the urethra. This will allow for adhesion of this surface to the tissue surrounding the urethra, thus securing it in place and not allow it to slide or wear the surface of the urethra. It is the further intention of the inventors to increase the intra-urethral pressure through the use of an equal circumferential pressure. This is applied by looping the flat strip of tissue around the urethra rather than kinking the urethra, as commonly done in prior art procedures. This equal circumferential pressure will be applied, preferably on the lower half of the urethra, over a larger portion of the urethral length than is common with present suture suspensions. It will be appreciated that the sling 20 may be longer, shorter, wider or thinner than illustrated in the present drawings.

It is to be further understood that even though numerous characteristics and advantages of various embodiments of the present invention have been set forth in the foregoing description, together with details of the structure and function of various embodiments of the invention, this disclosure is illustrative only and changes may be made in detail, especially in matters of shape, size and arrangement of parts, within the principles of the present invention, to the full extent indicated by the broad general meaning of the terms in which the appended claims are expressed.

What is claimed is:

1. A sling device for surgical implantation in a human recipient to support the urethra, the sling device comprising:
    an elongated strip of supple material which is biologically acceptable for implantation into the human recipient, the elongated strip of supple material having a looping limb and an extending limb extending from either side of a center portion, the center portion including a slot through which the looping limb can pass to thereby form a loop in the elongated strip of supple material for encircling the urethra to exert circumferential pressure on the urethra for the prevention of urinary incontinence.

2. The sling device of claim 1, wherein the material is selected from the group consisting of synthetic polymers, processed animal tissues, and combinations thereof, each of which are suitable for implantation in the human recipient.

3. The sling device of claim 2, wherein the material is a synthetic polymer selected from the group consisting of polytetrafluoroethylenes, expanded polytetrafluoroethylenes, polyethylene terephthalates and silicone elastomers.

4. The sling device of claim 2 wherein the material is a combination of a synthetic polymer and processed animal tissues, wherein the synthetic polymer is coated with animal tissue cells which are chemically cross-linked.

5. The sling device of claim 2 wherein the material is a processed animal tissue, the processed animal tissue being selected from the group consisting of porcine tissue, bovine tissue, ovine tissue, equine tissue and human tissue.

6. The sling device of claim 2, wherein the processed animal tissue is made from a tissue selected from the group consisting of tendons, ligaments and fibro serous tissues.

7. The sling device of claim 6, wherein the processed animal tissue is made from fibro serous tissues selected from the group consisting of dura mater, pericardium, peritoneum, tunica vaginalis and dermas.

8. The sling device of claim 2, wherein the processed tissues are tissues which have been cleansed, dehydrated, cross-linked and sterilized.

9. The sling device of claim 8, wherein the processed animal tissue is chemically cross-linked using a cross-linking agent selected from the group consisting of gutaradehyde, dialdehyde, dialdehyde starch and an epoxy compound.

10. The sling device of claim 1, wherein said looping limb and said extending limb each has an end portion spaced apart from a jointing portion which inter-connects said center portion with said looping limb and said extending limb, the sling device further comprising a first length of non-absorbable suture material which passes through said end portion of said looping limb distal to said center portion.

11. The sling device of claim 10, further comprising a suture needle with which the first length of suture material is engaged.

12. The sling device of claim 10, further comprising a second length of non-absorbable suture material passing through said end portion of said extending limb distal to said center portion.

13. The sling device of claim 12, further comprising a second needle through which the second length of non-absorbable suture material passes.

14. A sling device for surgical implantation in a human recipient to support the urethra, the sling device comprising:
    an elongated strip of material having variable dimensions including a thickness, a width and a length;
    wherein the length is greater than the width and the width is greater than the thickness;
    the elongated strip having a center portion and opposite first and second side portions interconnected with and extending away from the center portion, the side portions including an extending limb and a looping limb, the looping limb having a smallest width which is less than a largest width of the center portion, the center portion including a slot through which the looping limb can pass, thereby forming a loop in the elongated strip which encircles and supports the urethra to prevent urinary incontinence;
    wherein the material is a supple material which is sterile or can be effectively sterilized, and is otherwise biologically acceptable for implantation into the human recipient.

15. The sling device of claim 14, wherein the width of the looping limb is less than the width of the center portion.

16. The sling device of claim 15, wherein the slot has a width and length, the length of the slot being less than about 95% of the greatest width of the center portion and equal to or greater than the width of the looping limb.

17. The sling device of claim 16, wherein the elongated strip has shoulders extending from the looping limb to a point within the center portion where the width of the center portion is greater than the width of the looping limb, wherein the width of the center portion proximate at least one point proximate the shoulders is greater than the length of the slot.

18. The sling device of claim 14, wherein the material is selected from the group consisting of synthetic polymers, processed animal tissues, and combinations thereof, each of which are suitable for implantation in the human recipient.

19. The sling device of claim 18, wherein the material is a synthetic polymer selected from the group consisting of polytetrafluoroethylenes, expanded polytetrafluoroethylenes, polyethylene terephthalates and silicone elastomers.

20. The sling device of claim 18, wherein the material is a combination of a synthetic polymer and processed animal tissues, wherein the synthetic polymer is coated with animal tissue cells which are chemically cross-linked.

21. The sling device of claim 18, wherein the material is a treated animal tissue, the tissue being selected from the group consisting of porcine tissue, bovine tissue, ovine tissue, equine tissue and human tissue.

22. The sling device of claim 21, wherein the processed animal tissue is made from a tissue selected from the group consisting of tendons, ligaments and fibro serous tissues.

23. The sling device of claim 22, wherein the processed animal tissue is made from fibro serous tissues selected from the group consisting of dura mater, pericardium, peritoneum, tunica vaginalis and dermas.

24. The sling device of claim 21, wherein the processed tissues are tissues which have been cleansed, dehydrated, cross-linked and sterilized.

25. The sling device of claim 24, wherein the processed animal tissue is chemically cross-linked using a cross-linking agent selected from the group consisting of gutaraldehyde, glutaraldehyde starch, dialdehyde, dialdehyde starch and epoxy.

26. The sling device of claim 14, further comprising a first length of non-absorbable suture material, wherein the first length of suture material passes through a first end portion of the first side portion, distal to the center portion.

27. The sling device of claim 26, further comprising a suture needle with which the first length of suture material is engaged.

28. The sling device of claim 26, further comprising a second length of non-absorbable suture material passing through a second end portion of the opposite side portion.

29. The sling device of claim 28, further comprising a second needle through which the second length of non-absorbable suture material passes.

30. A method of reducing the incidence of involuntary urination in an incontinent human subject, wherein said incontinent human subject is a woman having a urethra, other tissues in general proximity to the urethra, and an abdominal rectus sheath, said method comprising the steps of:

(a) providing a sling device for surgical implantation into said incontinent human subject, said sling device including an elongated strip of supple material having a looping limb and an extending limb extending from a center portion, said center portion having a slot through which said looping limb can pass, said material being biologically acceptable for implantation into said incontinent human subject; and (b) surgically implanting said sling device in said incontinent human subject such that said looping limb passes through said slot to form a loop which encircles said urethra, such that said looping limb and said extending limb encircle said other internal tissues, and such that said looping limb and said extending limb are fixed together to exert sufficient tension to restrain said loop such that said urethra is biased upward, closer to said other internal tissues within said incontinent human subject, when said incontinent human subject is in a standing position.

31. The method of claim 30, said step of surgically implanting including the further sub-steps of:

encircling said abdominal rectus sheath with said looping limb and said extending limb; and fixing said looping limb and said extending limb together around at least a portion of said abdominal rectus sheath so as to provide sufficient tension to bias said urethra upward into an elevated position when said incontinent human subject is in said standing position.

* * * * *